United States Patent [19]

Southern

[11] Patent Number: 4,886,589

[45] Date of Patent: Dec. 12, 1989

[54] ELECTROPHORESIS METHOD AND APPARATUS FOR SEPARATING PARTICLES IN A SEPARATION MEDIUM

[75] Inventor: Edwin Southern, Oxford, England

[73] Assignee: The Chancellor, Masters and Scholars of the University of Oxford, Oxford, England

[21] Appl. No.: 57,972

[22] PCT Filed: Sep. 29, 1986

[86] PCT No.: PCT/GB86/00578
§ 371 Date: May 28, 1987
§ 102(e) Date: May 28, 1987

[87] PCT Pub. No.: WO87/02133
PCT Pub. Date: Apr. 9, 1987

[30] Foreign Application Priority Data

Sep. 30, 1985 [SE] Sweden ............................ 8504506

[51] Int. Cl.⁴ ...................... G01N 27/26; B01D 57/02
[52] U.S. Cl. .............................. 204/182.8; 204/183.1; 204/299 R; 204/300 R
[58] Field of Search ............ 204/299 R, 182.8, 182.9, 204/183.1, 300 R

[56] References Cited

U.S. PATENT DOCUMENTS

| | | | |
|---|---|---|---|
| 4,061,561 | 12/1977 | Fletcher et al. | 204/299 R |
| 4,148,703 | 4/1979 | Trop et al. | 204/182.8 |
| 4,473,452 | 9/1984 | Canton et al. | 204/299 R X |
| 4,737,251 | 4/1988 | Carle | 204/182.8 |

FOREIGN PATENT DOCUMENTS 8402001  5/1984  PCT Int'l Appl. ............. 204/182.8

Primary Examiner—John F. Niebling
Assistant Examiner—Ben C. Hsing
Attorney, Agent, or Firm—Nixon & Vanderhye

[57] ABSTRACT

Electrophoresis method and apparatus for separating particles in a separation medium (15) in which provided for driving the particles alternatively in different directions in the separation medium (15). The separation medium (15) is rotated at predetermined intervals in a plane between different rotary positions in one and the same electric field.

16 Claims, 1 Drawing Sheet

ELECTROPHORESIS METHOD AND APPARATUS FOR SEPARATING PARTICLES IN A SEPARATION MEDIUM

TECHNICAL FIELD

The invention relates to an electrophoresis method for separating particles in a separation medium, the particles being driven alternately in different directions in the separation medium, and an apparatus for carrying the method into effect.

BACKGROUND ART

Such electrophoresis methods and apparatuses are known from the U.S. Pat. Nos. 4,148,703 and 4,473,452. According to these two patents two electrode pairs are used, which are put under voltage alternately, and which are so located relative to the separation medium that the generated electric fields drive the particles to be separated alternately in different directions in the separation medium.

Besides two electrode pairs, a switching device is also required in such apparatuses to alternately put the electrode pairs under voltage. Such apparatuses are comparatively expensive.

Moreover, with electrodes on four sides of the separation medium the mutual positioning of the electrodes will be critical.

It should also be pointed out that no good separation will be obtained when the electrodes are located in such a manner that the electric fields generated by the respective electrode pairs are perpendicular to each other.

DISCLOSURE OF INVENTION

The object of the invention is to bring about a method and an apparatus which are less expensive than such methods and apparatuses known so far, and which, moreover, enable a better separation.

This is attained by the method according to the invention in that the separation medium is rotated at predetermined intervals in a plane between different rotary positions in one and the same electric field.

The apparatus according to the invention is mainly characterized in that it comprises a rotary support plate for supporting the separation medium, which support plate is provided between field generating means for generating an electric field, and a time-controlled driving member for rotating the support plate at predetermined intervals in a plane between different rotary positions in the electric field.

BRIEF DESCRIPTION OF DRAWING

The invention will be described more in detail below with reference to the drawing on which FIG. 1 schematicaly shows an embodiment of an apparatus according to the invention with a separation medium in a first rotary position.

DETAILED DESCRIPTION

Figure 1:
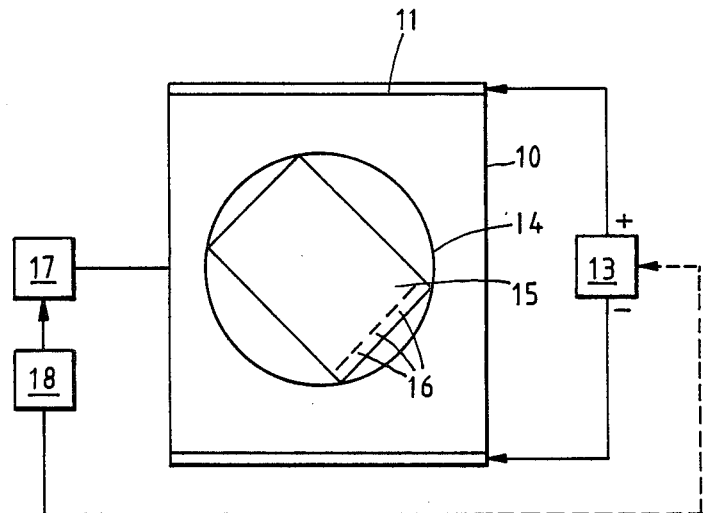

In FIG. 1 an embodiment of a conventional electrophoresis chamber is denoted 10. The chamber 10 shown in plan view is an open-top rectangular chamber made of an electrically insulating material, e.g. plexiglass. In the embodiment shown, electrodes 11 and 12 extend along the short sides of the chamber 10. These electrodes 11 and 12 are connected to the positive and the negative poles, respectively, of a D.C. source 13. In a manner known per se the electrophoresis chamber 10 is filled with a suitable buffer solution.

According to the invention a rotary support plate 14 is provided in the electrophoresis chamber 10, which support plate 14 is intended to support a separation medium, e.g. a gel plate 15, in which a separation of partibles in samples 16 applied to the gel plate 15, is to take place by means of the electric field generated between the electrodes 11 and 12.

The support plate 14 is rotatable by means of a driving member 17 known per se, e.g. an electric motor.

According to the invention the support plate 14 is rotated by means of the motor 17 around its centre axis at predetermined intervals by means of a timing circuit 18 between different predetermined rotary positions.

As indicated by a dashed line 19 the timing circuit 18 can be connected to the D.C. source 13 to disconnect the latter during the rotation of the support plate 14.

The timing circuit 18 can be set in such a manner that the rotary intervals as well as the rest intervals between the rotary intervals will have different lengths. Hereby it will be possible to make the angles between the different rotary positions for the support plate 14 unequally large.

Figure 2:
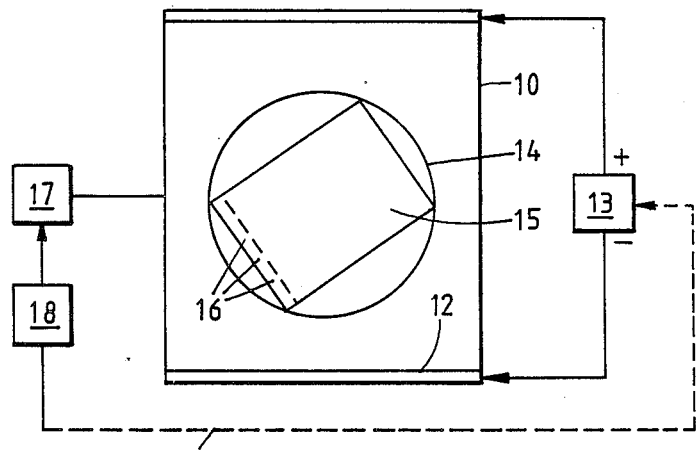
FIG. 2 shows the apparatus according to FIG. 1 with the separation medium in a second rotary position.

FIG. 2 fully agrees with FIG. 1 with the exception that the support plate 14 with the gel plate 15 has been rotated to a second rotary position which differs more than 90° from the rotary position shown in FIG. 1.

By rotating the separation medium in accordance with the invention, i.e. the gel plate 15 in the embodiment shown, a simplified and improved design from an electric point of view is obtained in comparison with the apparatuses known so far.

The importance of the rotary angle for the separation result will be illustrated below.

Two electrophoresis separations were carried out under identical conditions of voltage, buffer, temperature and sample. In both cases the samples were an oligomeric series of λ-DNA molecules.

The mobility, d, of the molecules in the gel, was calculated by means of the formula $$d = \frac{m}{\cos A},$$

where m is the mobility of the molecules along the central line of the gel, and

A is the angle between the central line of the gel and the electric field.

In one case the gel was rotated through 80° at intervals of 10 s, while the gel in the other case was rotated through 110° at intervals of 10 s.

In the case with a rotary angle of 80° the mobility of λ-DNA along the central line of the gel was measured to 2.8 μm/s and of the oligomers to between 2.4 and 2.55 μm/s. If these values are divided by cos 40° the following rates of movement through the gel during the pulse are obtained: 3.6 μm/s for the monomer, and between 3.1 and 3.3 μm/s for the oligomers.

In the case with a rotary angle of 110° the mobility of λ-DNA along the central line of the gel was measured to 2.1 μm/s. The oligomers were clearly resolved into a ladder pattern with mobilities from 1.8 μm/s for the dimer to 0.46 μm/s for the unresolved molecules larger than the octamer. Dividing by cos 55° gives 3.61 μm/s for the monomer and between 3.1 and 0.8 μm/s for the oligomers.

From this it is apparent that a rotary angle larger than 90° reduces the mobility of large molecules much more than smaller molecules.

I claim:

1. An electrophoresis method for separating particles in a separation medium, wherein the method comprises (a) creating an electric field, (b) effecting relative rotation between the separation medium and the electric field at predetermined intervals in a plane between different rotary positions and wherein the angle between the rotary positions is larger than 90°, and (c) allowing the particles to be driven in different directions in the separation medium by the electric field, whereby the particles are separated in the separation medium by virtue of their being driven in said different directions therein.

2. Method according to claim 1, wherein the intervals are of different lengths.

3. Method according to claim 1, wherein the angles between the rotary positions are variable.

4. Method according to claim 1, wherein the electric field is homogeneous.

5. Method according to claim 1, wherein the separation medium is rotated relative to a stationary electric field.

6. An electrophoresis method for separating particles in a separation medium, the method comprising the steps of (a) creating an electric field, (b) effecting relative rotation between the separation medium and the electric field between terminal rotary positions which are angularly spaced from one another by an angle greater than 90°, said step of effecting relative rotation being performed in discrete rotation intervals of predetermined unequal angular magnitude interspersed with rest intervals of predetermined duration in which no relative rotation occurs, (c) allowing the particles to be driven in different directions in the separation medium by the electric field, whereby the particles are separated in the separation medium by virtue of their being driven in said different directions therein.

7. Method according to claim 6, wherein the electric field is stationary, and the separation medium is rotated relative to the electric field.

8. An electrophoresis method for separating particles in a separation medium, wherein the method comprises (a) creating one and the same electric field, (b) effecting relative rotation between the separation medium and the electric field at predetermined intervals in a plane between different rotary positions and wherein the angle between the rotary positions is larger than 90°, and (c) allowing the particles to be driven in different directions in the separation medium by the electric field, whereby the particles are separated in the separation medium by virtue of their being driven in said different directions therein.

9. Electrophoresis apparatus for separating particles in a separation medium, comprising means for driving the particles alternately in different directions in a separation medium, wherein said means comprises field generating means for generating an electric field, a support plate for supporting the separation medium, said support plate being provided between said field generating means and a time-controlled driving means for effecting relative rotation between the support plate and the electric field generated by said field generating means at predetermined intervals in a plane between different rotary positions and wherein the angle between the rotary positions is larger than 90°.

10. Apparatus according to claim 9, wherein the field generating means are adapted to generate a homogeneous electric field.

11. Apparatus according to claim 9, wherein said time-controlled driving means includes means for controllably varying the lengths of the intervals.

12. Apparatus according to claim 9, wherein said driving means controllably varies relative rotation angles between the support plate and electric field.

13. Apparatus according to claim 9, wherein said driving means is operatively coupled to said support plate so as to effect rotation of said support plate relative to said electric field.

14. Apparatus for separating particles in a separation medium comprising:
    support means for supporting the separation medium in which said particles to be separated are disposed;
    electric field generating means for generating an electric field; and
    driving means for establishing terminal rotary positions which are angularly spaced from one another by an angle greater than 90°, and for effecting relative rotational motion between said support means and said electric field generating means between said terminal rotary positions; and wherein
    said driving means effects said relative rotation in discrete rotary intervals of predetermined unequal angular magnitude interspersed with rest intervals of predetermined duration in which no relative rotation occurs, whereby separation of said particles is achieved.

15. Apparatus according to claim 14, wherein said driving means is operatively coupled to said support plate so as to effect rotation of said support plate relative to said electric field.

16. Electrophoresis apparatus for separating particles in a separation medium, comprising means for driving the particles alternately in different directions in a separation medium, wherein said means comprises field generating means for generating one and the same electric field, a support plate for supporting the separation medium, said support plate being provided between said field generating means and a time-controlled driving means for effecting relative rotation between the support plate and the electric field generated by said field generating means at predetermined intervals in a plane between different rotary positions and wherein the angle between the rotary positions is larger than 90°.

* * * * *